(12) United States Patent
Neuberger et al.

(10) Patent No.: US 8,926,601 B2
(45) Date of Patent: Jan. 6, 2015

(54) LASER PLASMA MODULATOR SYSTEM FOR ENDOSCOPY AND ENDOCAVITARY SURGERY

(71) Applicants: Wolfgang Neuberger, Dubai (AE); Walter Cecchetti, Saonara (IT); Leonardo Cecchetti, Saonara (IT); Filiberto Zattoni, Padua (IT)

(72) Inventors: Wolfgang Neuberger, Dubai (AE); Walter Cecchetti, Saonara (IT); Leonardo Cecchetti, Saonara (IT); Filiberto Zattoni, Padua (IT)

(73) Assignee: Biolitec Pharma Marketing Ltd, F.T. Labuan (MY)

( * ) Notice: Subject to any disclaimer, the term of this patent is extended or adjusted under 35 U.S.C. 154(b) by 0 days.

(21) Appl. No.: 13/673,727

(22) Filed: Nov. 9, 2012

(65) Prior Publication Data

US 2013/0310819 A1 Nov. 21, 2013

Related U.S. Application Data

(63) Continuation of application No. 12/629,313, filed on Dec. 2, 2009.

(60) Provisional application No. 61/119,259, filed on Dec. 2, 2008.

(51) Int. Cl.
*A61B 18/22* (2006.01)
*A61B 18/04* (2006.01)
*A61B 18/26* (2006.01)
*A61N 1/44* (2006.01)

(52) U.S. Cl.
CPC ............... *A61B 18/22* (2013.01); *A61B 18/042* (2013.01); *A61B 2018/263* (2013.01); *A61N 1/44* (2013.01)
USPC ................... 606/15; 607/89; 606/10; 606/12; 372/6; 385/31; 398/196

(58) Field of Classification Search
CPC ............ A61N 5/06; A61B 18/18; H01S 3/30; G02B 6/42; H04B 10/04
USPC ......... 607/89; 606/15, 10, 12; 372/6; 385/31; 398/196
See application file for complete search history.

(56) References Cited

U.S. PATENT DOCUMENTS

| | | | |
|---|---|---|---|
| 5,057,099 A * | 10/1991 | Rink ............................... | 606/12 |
| 6,208,781 B1 * | 3/2001 | Neuberger et al. ............. | 385/31 |
| 6,271,944 B1 * | 8/2001 | Schemmann et al. ......... | 398/196 |
| 2004/0057471 A1 * | 3/2004 | Shevy et al. ..................... | 372/6 |
| 2005/0021013 A1 * | 1/2005 | Visuri et al. .................... | 606/15 |
| 2005/0288653 A1 * | 12/2005 | Lai et al. ......................... | 606/10 |
| 2007/0219601 A1 * | 9/2007 | Neuberger ...................... | 607/89 |

* cited by examiner

*Primary Examiner* — William Thomson
*Assistant Examiner* — Victor Shapiro
(74) *Attorney, Agent, or Firm* — Bolesh J. Skutnik; BJ Associates

(57) ABSTRACT

An improved system for safe and efficient generation of plasmas and vapors bubbles with continuous wave radiations and low levels of power densities, sufficient to treat medical pathologies and to avoid the creation damage to healthy tissue is provided. Transmission means in different configurations are used to achieve a high absorption in water, which is able to initiate plasma with low levels of power density. Once plasma and vapor bubbles are formed, they absorb other wavelengths in addition to the one that initiated it. Other wavelengths, more efficiently generated by diodes or diode pumped lasers, are added into the beam to improve treatment efficiency. This modulated plasma produces fast tissue ablation and good hemostasis effect with minimal overheating of remaining tissue. After plasma and high-energy vapors are generated, only laser radiation that passes through the plasma bubble directly interacts with soft tissues.

16 Claims, 4 Drawing Sheets

Figures

LASER PLASMA MODULATOR SYSTEM FOR ENDOSCOPY AND ENDOCAVITARY SURGERY

CROSS REFERENCE TO PRIORITY APPLICATION

This application is a continuation in part of U.S. Ser. No. 12/629,313, filed Dec. 2, 2009, entitled "Diode Laser Induced Vapor/Plasma Mediated Medical Procedures and Device" by Wolfgang Neuberger and Walter Cecchetti, which is incorporated by reference herein, and which in turn claimed the benefit and priority of U.S. Provisional Application Ser. No. 61/119,259 filed Dec. 2, 2008, entitled "Diode Laser Induced Vapor/Plasma Mediated Medical Procedures and Device" by Wolfgang Neuberger and Walter Cecchetti.

BACKGROUND OF THE INVENTION

1. Field of the Invention

The present invention is related to minimally invasive devices and methods for treatment of biological tissue. More particularly, the invention relates to surgical procedures mediated by diode laser induced modulated plasma in order to achieve specific effects on tissues.

2. Invention Disclosure Statement

Since laser technology was introduced in markets for medical procedures, numerous laser devices have been proposed for tissue removal. Laser energy can be used taking advantage of its different advantageous features. As a consequence, tissue can be ablated, vaporized, liquefied, coagulated, etc, through laser radiation by means of using different treatment parameters, such as power density on the tissue target, energy dose, and by selecting the specific wavelength, etc.

Laser energy can also lead to plasma formation on the matter. Plasma formation is achieved through fast matter ionization with optical breakdown, which is a non linear effect produced when laser radiation is strongly absorbed by irradiated matter and/or with high power density on the target.

Plasma formation is a very complex phenomenon; if the electromagnetic radiation impacts with the target and is absorbed strongly, if there is enough power density, plasma formation is triggered. An optical breakdown starts and an ionization of the matter rapidly expands, generating shockwave and a cavitation effect with crackling noise, if the target medium is water hot vapor bubbles also form. [M. H. Niemz, "Laser Tissue Interaction": Springer-Verlag ed. 2002—W. Cecchetti, Urology 63 (3), 2004]. A cavitation process with the vapour bubbles give further contribute to shockwave growth. As a consequence, by focusing laser energy on a target material such as a gas, liquid or solid, the latter may be damaged by the sequence of plasma formation with optical breakdown and shockwave generation.

If the target has a high absorption of the laser radiation, the plasma formation can occur even with low levels of laser power and also in continuous emission. Plasma and cavitation phenomena are both associated with strong photo-thermo-ablative and photo-mechanical effects. Inside plasma bubbles, high temperatures of over a thousand degrees arise. The presence of cavitation effects is always associated with shock waves with the typical crackling noise. One example of how this can be achieved is by providing an initial pulse as for instance in the FREDDY device (in this case generated by a flash lamp pumped frequency doubled pulsed Nd-YAG laser). The plasma produced by FREDDY laser, that due to the short duration of pulses, has high photomechanical effect and insignificant thermo ablative effect.

According to the afore-mentioned mechanism of action, laser energy can be applied in two different ways to achieve tissue removal (by means of plasma formation). Indirectly, by focusing it upon a target placed between laser beam and tissue, or directly on target tissue in order to achieve its removal. In the first case, laser energy is transmitted through an optical fiber immersed in water, generating plasma bubbles on fiber tip that produce the damage of the entire tissue that is located in the expansion area of the plasma bubbles.

In U.S. Pat. No. 5,224,942, Beuchat et al. disclose a method and apparatus using laser energy for destroying body tissue which includes a handpiece comprising a surgical tip assembly which is driven by means of laser to achieve optical breakdown, plasma formation and shockwave generation to emulsify or destroy body tissue. As laser is focused on a target (placed inside the handpiece) which vibrates due to plasma formation, mild energy is applied to tissue, which is only emulsified by mechanical vibration of handpiece tip. As a consequence, versatility of this system is limited as it is aimed at treating soft tissue.

U.S. Pat. No. 5,324,282 by Dodick et al., teaches a system based on similar principles. Pulsed laser energy is discharged to strike a metal target, which acts as a transducer converting the electromagnetic energy into shockwaves that are directed to the tissue to be treated. The mechanical shockwaves cause the tissue to fracture.

In U.S. Patent Publication No. 2004/0167504 Thyzel et al. disclose a surgical needle for fracturing tissue comprising a distal operating port which holds tissue. Pulsed laser energy is applied to a target through an optical fiber, generating shockwaves due to plasma formation from the optical breakdown of target, impinging on the tissue to be fractured. This patent is mainly focused on fracturing tissue, so here again system versatility is limited.

Afore-mentioned patents are founded on plasma formation upon a target material, which converts optical breakdown into mechanical vibrations. As a consequence, energy loss occurs in this transduction, diminishing treatment efficacy. Furthermore, mechanical vibrations are not selective with the tissue to be treated, so effects on other tissue rather than tissue to be treated may appear. In other words, not only desired tissue may be affected by vibrations.

When laser radiation is directly focused on tissue in order to achieve its removal, target for radiation is now tissue itself Usually, tissue to be removed is surrounded by liquid and illuminated with laser radiation above a threshold intensity level, it generates plasma bubbles with very high internal temperatures. Thus, tissue undergoes rapid thermal ablation, associated with the mechanical damage of the cavitation effect (example Ho-YAG laser). This method is widely used in order to break calculi, bones, and calcified tissue within the body. This way stones have been fractured by the shockwaves created due to the collapse of bubbles initiated by plasma formation at the tip of fiber optics delivering laser pulses from flash lamp pumped, frequency doubled YAG lasers (FREDDY).

For instance, plasma has been used in medical treatments in the form of ionized Argon gas for the ablation of mucosal layers; TURis resectoscope of Olimpus uses a plasma bubble, generated by electrical device, for the ablation of prostatic tissue for the BPH treatment.

In U.S. Pat. No. 5,071,422, Watson et al. disclose a method for breaking down material within the body, based on a pulsed dye laser source. Optical fiber is inserted in the area to be treated, which is surrounded with liquid and then radiated with pulsed dye laser energy in order to achieve fragmentation by means of shockwaves. This invention basically discloses calculi and stone fragmentation. But if dye laser radiation is not absorbed by stones, plasma formation will not occur and laser lithotripsy will not be effective. The plasma produced by a dye laser produces mainly photomechanical effects. Furthermore, as a pulsed dye laser source is used, frequent maintenance may be required as this source is not a solid-state laser.

U.S. Pat. No. 5,963,575 by Müller et al., discloses a Q-switched laser system for laser lithotripsy. The system incorporates longer pulse duration, increasing plasma formation and consequently shockwave production. Laser source is preferably a Nd:YAG laser, which is a ionic crystal source. As a consequence, it has low efficiency, large dimensions, and needs liquid cooling. Moreover, it requires alignment, as laser radiation is conveyed to the treatment zone by means of minors instead of optical fibers. Furthermore, this technology lacks precision compared to other laser technologies.

In U.S. Pat. No. 4,960,108, Reichel et al. teach a laser-induced lithotripter in which pulsed laser radiation in the vicinity of infrared region is concentrated at a concrement to be destroyed which is surrounded with an aqueous rinsing liquid. Concrement is destroyed by breakdown (plasma) of rinsing liquid, giving rise to shockwave and cavitation. Rinsing liquid includes a metal compound which lowers the energy required for said breakdown.

All previous-mentioned patents only disclose use of laser sources that may be usually voluminous, inaccurate, inefficient and/or requiring frequent maintenance.

Due to the disadvantages and lack of versatility of current plasma formation techniques, a need exists for a device that provides a fast and safe alternative to address their shortcomings.

OBJECTIVES AND BRIEF SUMMARY OF THE INVENTION

It is an objective of the present invention to provide a device to generate plasma and vapors bubbles for medical applications by means of laser diodes with continuous emission, that have very high absorption of radiation by the aqueous medium, or other liquid medium.

It is also an objective of the present invention to use a laser radiation strongly absorbed by the aqueous medium to form bubbles of plasma and modulate this plasma with another laser radiation released simultaneously in the same optical fiber.

It is also an objective of the present invention to provide a device which utilizes advantageous features of diode laser wavelengths to generate plasma and modulate plasma bubbles for medical applications, leading to more efficient and safer treatments.

It is another objective of the present invention to provide a system that modulates the thermal energy release for medical applications by means of laser diodes which enhances versatility of treatments that can be carried out.

It is yet another objective of the present invention to provide a method to generate and modulate plasma bubbles for medical applications by means of laser diodes using power levels and power densities sufficient to treat medical indications yet minimizing damage to healthy tissue.

Briefly stated, the present invention provides an improved system for safe and efficient generation of plasmas and vapors bubbles with continuous wave radiations and low levels of power densities, sufficient to treat medical pathologies and minimizing overheating of healthy tissues. Transmissions means in different configurations are used to achieve a high absorption in water, which is able to initiate plasma with low levels of power density. Once plasma and vapor bubbles are formed, means for modulating the thermal energy release by plasma and bubbles are provided. In a preferred embodiment, the means is the delivery/addition of at least one laser wavelength generated by diodes or diode pumped lasers, which is sufficiently absorbed by the plasma/bubble and as a consequence improve treatment efficiency. This modulated plasma produces fast tissue ablation and good hemostasis effect with minimal overheating of remaining tissue. After plasma and high-energy vapor bubbles are generated, only laser radiation that passes through the plasma bubble directly interacts with soft tissues.

The above, and other objects, features and advantages of the present invention will become apparent from the following description read in conjunction with the accompanying drawings.

DETAILED DESCRIPTION OF PREFERRED EMBODIMENTS

Diode lasers have been used in medicine due to the favorable laser tissue interaction of the respective wavelength providing absorption and coagulation as well as vaporization. For equal output power, diode lasers are smaller, lighter, air cooled, with high reliability and without alignment and maintenance requirements, especially compared to solid state lasers, dye lasers or frequency-doubled solid state lasers.

Some of the before-mentioned techniques limitations and problems can be overcome by using the inherent benefits of laser diodes (such as efficient power generation from a reliable and compact solid state device) in order to generate plasma and vapor bubbles for medical applications with continuous wave radiation and power levels and power densities sufficient to treat medical pathologies and minimizing damage to healthy tissue.

As mentioned previously, high absorption in (aqueous) medium is required to initiate plasma/vapor bubbles formation with continuous wave radiation and the right level of power density on the target. However it is possible to use different shaped fiber tips to change (modulate) the plasma bubbles size as well: an example is the use of very thin fibers tip immersed in an aqueous environment to increase the power density and internal temperature of plasma bubbles as in lithotripsy. The large fiber tips (conical or twister) increase the bubbles dimension which produce a greater tissue ablation, while reducing (modulate) the internal temperature of plasma to limit overheating on healthy tissues.

When continuous wave radiation with high absorption in water is delivered through the fiber immersed directly in aqueous environment, water molecules on the fiber tip are highly and rapidly heated. The very fast and extremely high heating causes a ionization with rapid expansion, producing plasma bubbles, which collapse a few millimeters away and after few milliseconds, producing glow and crackling noise. Successively, after few milliseconds, the process repeats and the crackling noise can be heard again. These bubbles reach an interior temperature of over a thousand degrees. As a consequence, they have a considerable thereto-ablative effect and release their thermal energy in the surrounding water. So the hemostatic effect on soft tissue is not related to direct laser interaction with the tissue itself. Instead, it occurs due to the thermo spray effect of vapor and hot water generated around plasma bubbles, which releases thermal energy in the water. Hence, by modulating and controlling the size, shape and lifetime of the plasma bubble, the extent and quality of the thermo-spray effect of the vapor and the hot water generated around the plasma bubble are also controlled. Consequently, by modulating the output power of the Plasma Modulator Laser different degrees of thermo-ablative and hemostatic effects are provided.

Figure 1A:
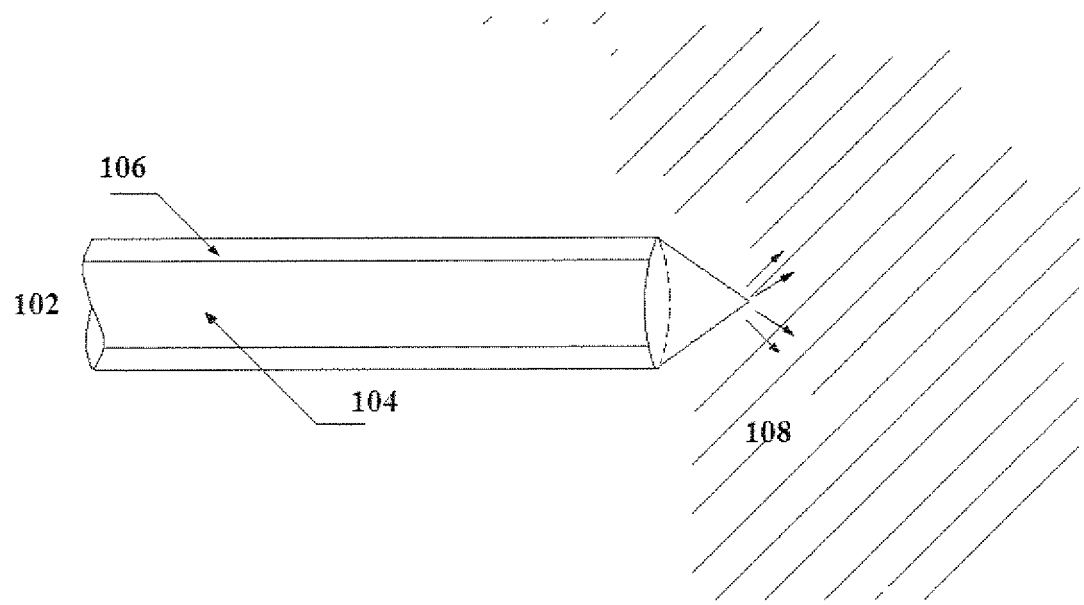
FIGS. 1a and 1b depict a preferred embodiment of the present invention in which a plasma bubble is produced due to laser radiation.
Figure 1B:
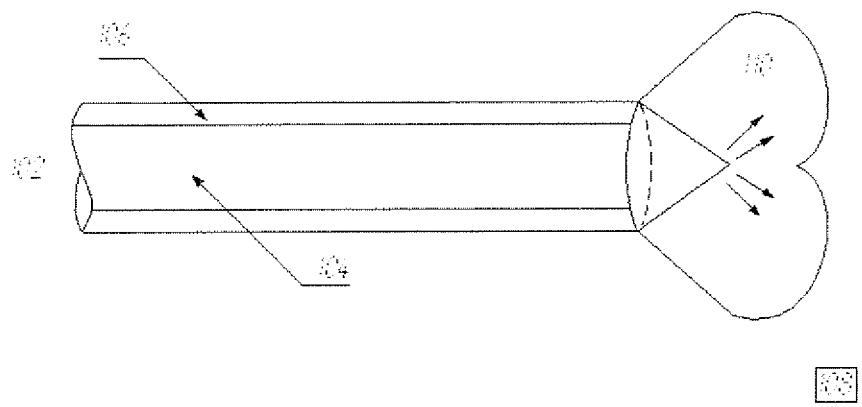

FIGS. 1a and 1b depict one embodiment of the present invention in which the diode laser device, also referred to as Plasma Modulator Laser, is coupled to optical fiber 102 comprising core 104 and clad 106, which emits laser energy to liquid 108 in order to produce plasma formation. Bubble 110 will be formed provided the wavelength and power are adequately chosen in order to create sufficient absorption in the environment. For instance, as 1470 nm wavelength is highly absorbed in water, it is appropriate for this purpose because it is able to generate plasma on the fiber tip immersed in water with continuous wave radiation and very low power densities.

In a preferred embodiment, optical fiber 102 tip is conically shaped.

In another preferred embodiment, optical fiber tip is bent such as a Twister™ fiber and is coupled to the Plasma Modulator Laser which operates at two laser wavelengths. Fiber tip diameter is preferably large in order to achieve larger plasma bubbles which produce a greater tissue ablation. The first laser wavelength delivered through the optical fiber is a wavelength highly absorbed by water which is capable of initiating plasma and high-energy vapor bubbles at the tip with low power levels. Once plasma and high-energy vapor bubbles are formed, a second laser wavelength is delivered through the optical fiber for modulating the thermal energy released of the plasma and vapor bubbles. As a consequence, other wavelengths more efficiently generated by diodes or diode pumped lasers (for instance, 980 nm) are used for modulating the plasma and vapor bubbles in order to improve treatment efficiency while avoiding or diminishing overheating of the healthy tissue. In a preferred embodiment, plasma and/or high-energy vapors bubbles are formed with the delivery in continuous mode of a first laser wavelength highly absorbed by water and are modulated with a second laser wavelength. As an example, the first laser wavelength is of about 1470±50 nm and the second is of about 980±30 nm. The modulated combination of these laser wavelengths causes mainly a thermoablative effect with the plasma formation and a coagulation effect due to thermospray at the fiber tip. In summary the 1470 nm CW diode laser wavelength, strongly absorbed by water, forms plasma on the fiber tip immersed in the aqueous medium; the wavelength of the 980 nm diode simultaneously emitted, is absorbed (around 70%*) by the plasma and increases its dimensions; the residual 30% of 980 nm radiation comes out from the plasma and interacts with the tissue, producing an additional soft hemostasis. Hence, the predetermined ratio between the two wavelengths wherein one modulates the other, changes (modulates) the dimensions and the internal temperature of the plasma bubble. In one embodiment, an efficient combination between the two wavelengths is 30% of 1470 nm and 70% of 980 nm. A further modulation of the plasma bubble can be obtained by changing the ratio between the two radiations; moreover the use of fibers with different irradiation geometries causes a further modulation of the power density, changing the plasma bubbles size.

In vitro tests showed that when plasma and vapor bubbles are in place with 100 W of emitting power, there is a mainly thermo-ablative effect within 5 mm from fiber tip, (FIG. 9) and a coagulation effect due to thermospray within 9 mm from fiber tip. The residual 30%*(21 W) of the 980 nm radiation contributes to a soft homeostasis within 1 mm in the remaining tissue. Since the medium has a very high absorption coefficient of the radiation it is the true mediator of interactions between radiation and tissue.

By choosing the pattern of modulation of the laser wavelengths delivered by the Plasma Modulator Laser, different degrees of coagulation are obtained. In one embodiment, the modulated combination of laser wavelengths is used for determining a desired coagulation degree by using it for determining the characteristics of the plasma and vapor bubbles. The plasma bubbles generated by the Plasma Modulator Laser produce a very hot medium, which releases its high thermal energy on the surrounding medium. Other degrees of coagulation are obtained in the tissue by modulating the residual of the second laser radiation that pumps the plasma but is poorly absorbed by the medium, as the 980 nm. In other embodiments other degrees of coagulation are obtained in the tissue with the modulated combination of laser wavelengths by generating plasma bubbles that emit certain parts of the spectrum which are sufficiently absorbed by the tissue, by transmitting to the tissue certain parts of the original laser radiation, and by controlling the interaction of the high-energy vapors with tissue.

According to afore-mentioned explanation, this invention accomplishes substantial versatility regarding to the variety of medical treatments that can be performed by its means.

As a preferred embodiment, the invention is practiced in tissue containing sufficient quantities of water or in an aqueous environment as saline solution or other biocompatible liquids.

Figure 2A:
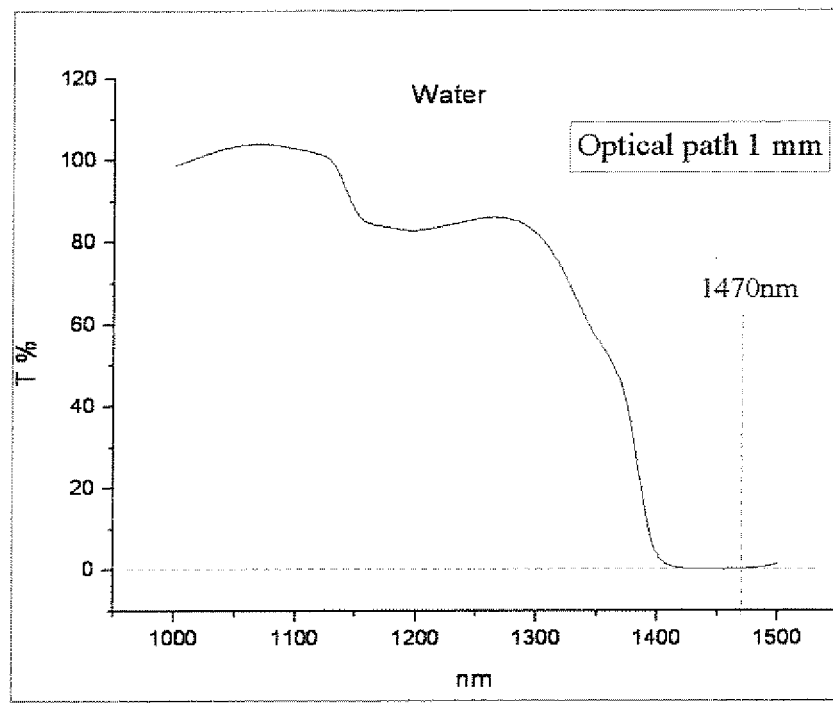
FIGS. 2a and 2b shows graphs representing water and blood absorption respectively of wavelengths between 980 nm and 1470 nm.
Figure 2B:
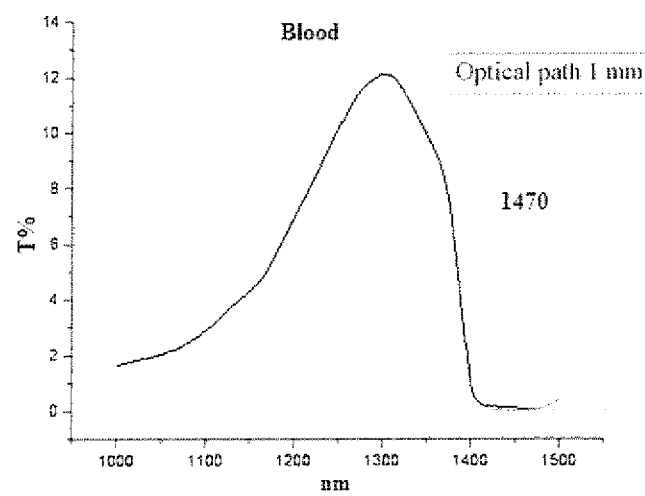
Figure 3:
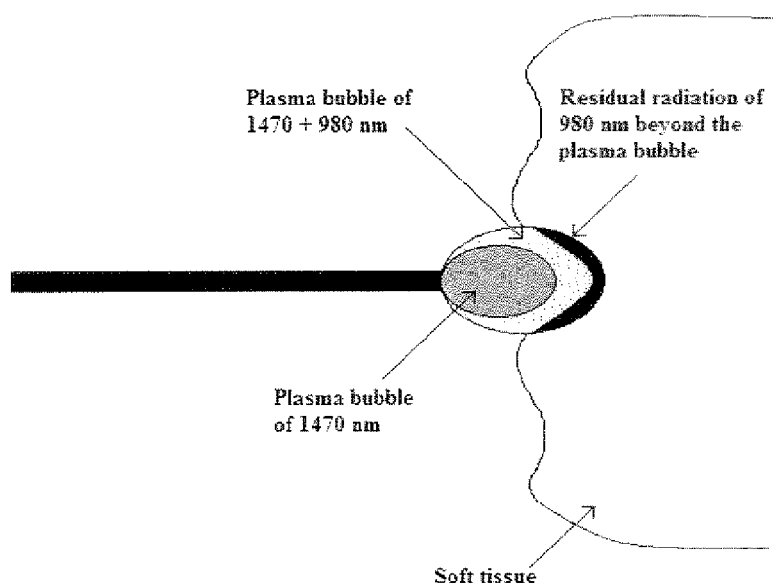
FIG. 3 shows a high power Plasma Modulator Diode Laser using 1470 nm radiation to form plasma bubbles, and 980 nm radiation to pump and expand the plasma bubbles.

A laser plasma modulator was designed with two parallel diode laser sources able to deliver one or more simultaneous wavelengths in the same optical fiber, for instance 1.470 nm together with 980 nm. Absorption spectra of water and blood from 980 nm to 1470 nm is shown in FIGS. 2a and 2b. At 1470 nm there is high absorption in water, thus leading to formation of high energy plasma bubbles at fiber tip associated with cavitation effect with vapor and hot water bubbles. This effect is able to produce fast ablation of soft tissue associated to a coagulation effect with good hemostasis. At 980 nm there is low absorption in water, but high absorption in blood, thus good hemostatic effect can be achieved. With the Plasma Modulator Laser used in treatment of Benign Prostatic Hyperplasia (BPH), fast ablation on prostatic tissue with a good hemostatic effect with minimal thermal damage on the surrounding tissues can be accomplished. The residual 30% of the 980 nm (21 W over a 100 W total) contributes to a soft hemostasis within 1 mm in the remaining tissue.

Effects produced by the optical fiber immersed in water, and connected to a 1470 nm diode laser source, were verified to cause plasma formation thresholds that are very close to those needed for producing similar effects with a 1940 nm diode laser. Furthermore, 1470 nm diode laser produces similar effects in water as does the CW thulium laser, and therefore similar effects in biological matter. However, diode lasers have many advantages when comparing to ionic crystal lasers such as thulium. For instance, 1470 nm diode laser has currently an efficiency of 25% whereas thulium laser's efficiency is 8%. In addition, for equal output power, diode lasers are smaller, lighter, air cooled, more reliable and with no alignment and maintenance requirements.

When using a diode laser emitting at 1470 nm in CW (continuous) mode, fiber tip immersed in water creates high energy bubbles, which were observed, after investigation, to be plasma bubbles.

The 1470 nm radiation impinges water molecules in contact with fiber tip, leading to fast heating, with cavitation bubble formation, and thermo spray of boiling hot water. All electromagnetic energy is converted into thermal energy due to the high absorption. Thus, an optical path of 1 mm of water absorbs almost 100% of radiation (FIG. 2a, 2 b).

One advantage of the plasma bubbles produced by 1470 nm diode is that these have internal thermal energy lower than bubbles produced by the pulsed holmium laser, which works with peak powers in the order of kilowatts. This fast heat-up produces a rapidly growing amount of boiling hot water and creates a plasma bubble and consequently shockwave production. After a few milliseconds, the process occurs again with an associated crepitating noise. The plasma bubbles produce similar effects as sparkling plasma bubbles, with shockwave noise but with lower energy. These bubbles are highly destructive due to thermo ablative effects, and their associated thermal energy affects surrounding water within a radius of few millimeters. Consequently, 1470 nm diode laser also contributes to hemostatic effect, which is not produced by direct interaction of radiation with biological tissue, but is mediated by water. Hemostatic effect is produced by a thermo spray of boiling hot water, created on the fiber tip from the cavitation bubble which, when released, delivers thermal energy to the surrounding water. Considering the previous paragraphs, plasma bubbles were created with continuous wave sources and a thermo-ablation effect with high energy was achieved. This is an especially novel conception when compared to prior art, which discloses generally only pulsed laser sources.

Clinical trials and vitro tests with histological results using a Plasma Modulator laser have proven the efficacy of combining at least two wavelengths for achieving effective plasma formation for desired tissue effects, particularly with 1470 nm and 980 nm diode lasers. When the 1470 nm wavelength is delivered by a thin optical fiber immersed in water, it produces plasma bubbles with threshold levels as low as 2 W of emitted power in 600 μm fiber. The plasma releases its thermal energy in water and produces vapor and hot water bubbles, capable of coagulating tissues up to 5 to 8 mm from the fiber tip.

The plasma produced by 1470 nm is capable of producing a fast ablation of soft tissue with thin coagulation as well as rupture of hard tissue (such as urinary stones, calculi). The 980 nm wavelength has excellent absorption in blood and less absorption in water (FIG. 2). Hence, the 980 nm wavelength is used for pumping the plasma thus increasing the dimension of the bubbles and the hemostatic effects with a clear whitening. A wavelength of 980 nm alone can penetrate 2-4 mm into soft tissue.

With the Plasma Modulator Laser of this embodiment, the 1470 nm radiation produces a plasma bubble on the fiber tip immersed in water. Then, a simultaneous emission of 980 mm wavelength in the same fiber arrives into the plasma bubble, it is absorbed at around 70% and the residual 30% exits from the plasma bubble. Consequently, 70% of the 980 nm energy is converted into plasma, and 70% of this wavelength works as a pump for the plasma bubble produced by the 1470 nm wavelength. The residual 30%, of the 980 nm, beyond the plasma bubble, reaches the tissue and produces further hemostasis. Thus, clinical and in-vitro tests show that the Plasma Modulator Laser delivers low power of 1470 nm wavelength, in order to generate a plasma bubble, and with the 980 nm wavelength, which has a lower cost and higher efficiency, provokes the amplification and growth of this plasma bubble (FIG. 7).

With the Plasma Modulator Laser used in treatment of Benign Prostatic Hyperplasia (BPH), fast ablation on prostatic tissue with a good haemostatic effect with minimal thermal damage on the surrounding tissues can be accomplished. In our tests the Plasma Modulator Laser combines the two wavelengths in a ratio of 30% and 70%, which for a total emission of 100 W CW corresponds respectively to 30 W at 1470 nm and 70 W at 980 nm.

The device was also designed with the possibility to select a single wavelength for performing specific surgical applications.

Thus, the plasma modulator laser allows operating with fast ablation on the soft tissues and minimal overheating of the healthy tissues, and compared to other high power lasers (over 100 W) used in BPH treatment there is not the risk of overheating the healthy tissues that cause post operatory irritative symptoms. Clinical trials showed the excellent efficacy of the Plasma Modulator Diode Laser to perform easy and faster treatments in BPH procedures. The possibility of using an optical fiber capable of emitting radiation on a larger tissue surface was conceived, in order to obtain more tissue ablation in each sweep. In a preferred embodiment the optical fibers coupled to the Plasma Modulator Lasers are 1000 μm conical fibers instead of side firing fibers which allow using the fast thereto-ablative effects. After each sweep a large and clean furrow is obtained, without bleeding. The furrow obtained is larger than that produced by side firing fibers (FIG. 7).

Figure 4:
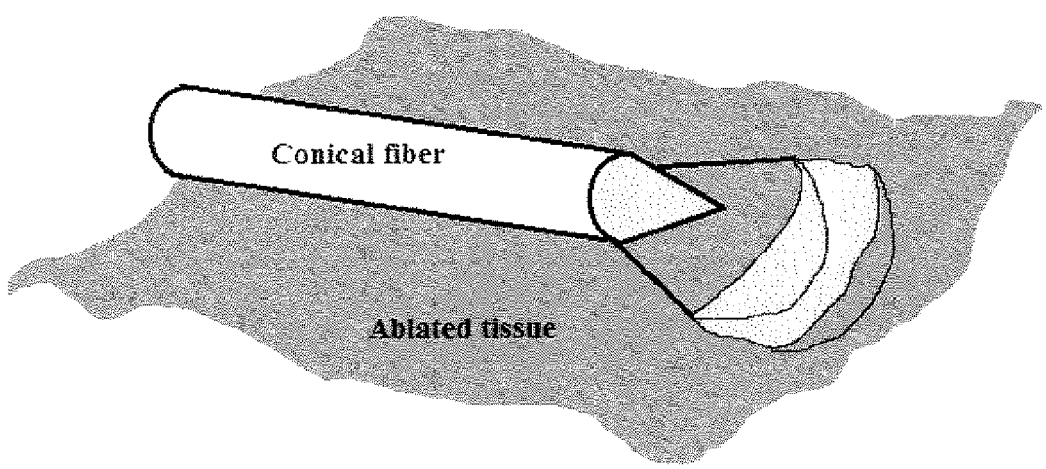
FIG. 4 depicts burrow production on soft tissue by means of laser radiation delivered through a conical tip optical fiber.

FIG. 4, shows conical fiber that produced a furrow on soft tissue.

With conical fibers, ablation efficacy was combined with a good hemostasis effect, allowing for a complete BPH treatment faster than other similar laser procedures, and faster even than the other laser and TURP procedures for BPH treatment.

Figure 5:
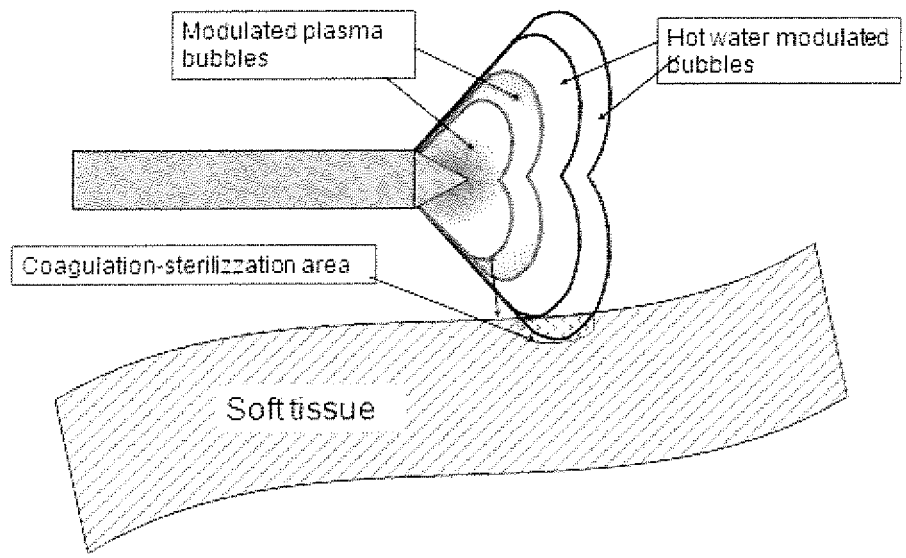
FIG. 5 shows bubbles generated by modulated laser plasma on conical fiber tip.

FIG. 5 shows bubbles generated by modulated laser plasma on conical fiber tip.

In another preferred embodiment asymmetric off-axis emitting fibers may be employed, such as twister fibers disclosed in U.S. Patent Publication No. US-2011/0160713 by Neuberger. These fibers allow better twistability and maneuvering possibilities.

Figure 6:
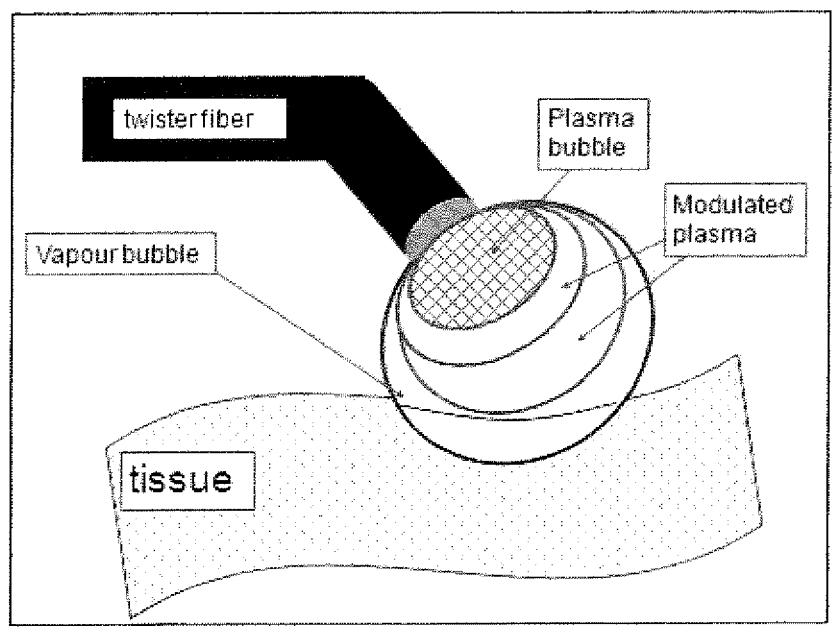
FIG. 6 shows a twister fiber tip immersed in water linked with Plasma Modulator Laser.

FIG. 6 shows twister fiber tip immersed in water linked with Plasma Laser Modulator.

For BPH treatment of prostates of 50 gr, when using power setting of 110 W, total treatment time for the ablation of prostatic adenoma was about 25 min. It must be considered that the same prostate dimension can be treated with TURP modalities in about 30 minutes, slower than the treatment with plasma modulator diode laser.

Patients in post treatment referred no pain or any other inconvenient (see FIG. 7). No bleeding was observed and the catheter was removed in the same day.

In another preferred embodiment, other combinations of laser sources can be used to achieve diode pumped laser device to generate plasma utilizing plasma ignition means and pulse energizing means. For instance, a double core fiber in which the ignition radiation is guided in the single mode core and the radiation used to maintain and enhance the pulse is guided into the surrounding second core. The single mode or near single mode radiation comes from a fiber laser at 1550 nm, which is diode pumped or a q-switched, and the fiber elongated pulse of a diode pumped green laser, and radiation for pulse maintenance and enhancement, wherein the major part of the energy comes from a diode laser. The 1550 nm pulses can be generated from 915-980 or 1480 laser diode pumps Having described preferred embodiments of the invention with reference to the accompanying drawings, it is to be understood that the invention is not limited to the precise embodiments, and that various changes and modifications may be effected therein by skilled in the art without departing from the scope or spirit of the invention as defined in the appended claims.

What is claimed is:

1. A plasma modulator laser system for endoscopy and endocavitary treatment comprising:
   a first laser source operating in continuous mode and emitting a first continuous wave laser wavelength that is highly absorbed by water, generating a plasma bubble;
   a second laser source delivering a second laser wavelength modulating dimensions and internal temperature of the plasma by absorbing a portion of radiation at the second laser wavelength in the plasma bubble; another portion of the radiation at the second laser wavelength propagating through the plasma bubble;
   at least one waveguide optically coupled to the first and second laser sources;
   wherein the first continuous wave laser wavelength and the second laser wavelength are combined in a predetermined ratio, the predetermined ratio selected for modulation of the plasma bubble.

2. The laser system according to claim 1, wherein said first continuous wave laser wavelength is of 1470+/−50 nm and said second laser wavelength is of 980+/−30 nm.

3. The laser system according to claim 2, wherein part of said laser wavelength of 980+/−30 nm modulates plasma bubble, and the remaining percentage of said laser wavelength of 980+/−30 nm reaches the tissue at said treatment site to achieve hemostatic effect.

4. The laser system according to claim 1, wherein said first laser source is a low power laser source.

5. The laser system according to claim 1, wherein said second laser source is a low cost and efficient diode laser source.

6. The laser system according to claim 1, wherein said second laser source operates in pulsed mode, in continuous mode or in a combination of these modes.

7. The laser system according to claim 1, wherein at least one of said first and second laser sources is a diode laser source operating at a laser wavelength selected from 980+/−60 nm, 1470+/−60 nm, and 1940+/−60 nm.

8. The laser system according to claim 1, wherein said first continuous wave laser wavelength and second laser wavelength are delivered simultaneously at different power densities.

9. The laser system according to claim 8, wherein said first continuous wave laser wavelength and second laser wavelength are selected from the group of 980 nm and 1470 nm; 980 nm and 1940 nm; and 1470 nm, 1940 nm and 980 nm.

10. The laser system according to claim 1, wherein said waveguide has diverse irradiation geometries and dimensions, wherein said geometry and dimension changes the plasma bubble dimension, the plasma bubble temperature, and/or the laser power density on said treatment site.

11. The laser system according to claim 10, wherein said waveguide is an optical fiber.

12. The laser system according to claim 11, wherein said optical fiber has a fiber tip selected from the group of thin tips, conical tips and asymmetric off-axis emitting tips.

13. The laser system according to claim 12, wherein said optical fiber has a 1000 μm diameter conical fiber tip.

14. The laser system, according to claim 11, wherein said optical fiber has a concentric core structure, wherein one of the first continuous wave laser wavelength or second laser wavelength travels in an inner core and the other of the first continuous wave laser wavelength or second laser wavelength is transmitted in an outer core.

15. The laser system according to claim 1, wherein said first laser is a fiber laser and said second laser is a pump laser for said fiber laser, and wherein beams from both lasers are transmitted by said at least one waveguide.

16. The laser system according to claim 15, wherein said fiber laser emits at about 1550 nm, and said pump laser emits at either about 915-980 nm or at about 1480 nm.

* * * * *